United States Patent [19]
Dobrovolny

[11] Patent Number: 5,792,046
[45] Date of Patent: Aug. 11, 1998

[54] CAMMED RETRACTOR CLAMP

[75] Inventor: Walter Dobrovolny, St. Paul, Minn.

[73] Assignee: Minnesota Scientific, Inc., Minneapolis, Minn.

[21] Appl. No.: 603,901

[22] Filed: Feb. 22, 1996

[51] Int. Cl.⁶ ................................. A61B 17/00
[52] U.S. Cl. .............. 600/234; 403/374; 403/DIG. 8
[58] Field of Search ...................... 600/234, 227;
403/374, 409.1, DIG. 8, 321, 324; 248/229,
231.3, 289.1, 291, 316.2, 541; 24/67.1,
834, 516, 540, 541

[56] References Cited

U.S. PATENT DOCUMENTS

| | | | |
|---|---|---|---|
| 1,084,379 | 1/1914 | Wile | 403/374 X |
| 1,464,308 | 8/1923 | Copony et al. | 403/374 X |
| 1,839,726 | 1/1932 | Arnold | 600/234 X |
| 2,893,378 | 7/1959 | R.L. Cooper . | |
| 3,221,743 | 12/1965 | Thompson et al. . | |
| 4,355,631 | 10/1982 | LeVahn . | |
| 4,497,092 | 2/1985 | Hoshino . | |
| 4,617,916 | 10/1986 | LeVahn et al. . | |
| 4,718,151 | 1/1988 | LeVahn et al. . | |
| 4,786,022 | 11/1988 | Grieshaber . | |
| 4,949,707 | 8/1990 | LeVahn et al. . | |
| 5,020,195 | 6/1991 | LeVahn . | |
| 5,080,088 | 1/1992 | LeVahn . | |
| 5,242,240 | 9/1993 | Gorham | 403/391 |

*Primary Examiner*—Jeffrey A. Smith
*Attorney, Agent, or Firm*—Kinney & Lange, P.A.

[57] ABSTRACT

A surgical support structure joint includes a shaft having an axis, a first support member rotatably supported about the axis of the shaft and a camming member coupled to the first support member. The camming member is movable between a first clamped position and a second unclamped position. In the first clamped position, the camming member applies greater force to the first support member than in the second unclamped position to prevent rotation of the first support member in the first clamped position and to permit rotation of the first support member in the second unclamped position.

18 Claims, 3 Drawing Sheets

5,792,046

CAMMED RETRACTOR CLAMP

BACKGROUND OF THE INVENTION

The present invention relates to a surgical support structure. In particular, the present invention relates to a clamping mechanism for a surgical support structure such as a retractor support.

In abdominal and chest surgery, it is customary to use a retractor that is mounted to a retractor support that extends over an operating table. The retractor is used to hold back tissue proximate a surgical incision enabling the surgeon to work in areas such as the abdominal area or chest cavity.

Retractors typically include a blade and a handle which is typically a shaft to which the blade is attached. The retractor is attached to the retractor support by some type of clamping mechanism that engages the handle of the retractor.

It is desirable that the retractor be movable since the position of the retractor will depend on the surgery being undertaken and the particular patient. In addition, it is desirable that the position and orientation of the retractor be easily movable and adjustable during surgery.

SUMMARY OF THE INVENTION

The present invention is a surgical support structure joint for a surgical support structure such as a retractor clamp. The joint includes a shaft having an axis, a first support member rotatably supported about the axis of the shaft and a camming member coupled to the first support member. The camming member is movable between a first clamped position and a second unclamped position. The camming member applies greater force to the first support member in the first clamped position than in the second unclamped position to prevent rotation of the first support member in the first clamped position and to permit rotation of the first support member in the second unclamped position.

In a preferred embodiment of the present invention, the first support member includes a first leg portion and a second leg portion rotatably supported about the shaft. The first leg portion and the second leg portion define a clamping bore therebetween. In the first clamped position, the camming member forces the first and second leg portions towards one another to reduce the diameter of the clamping bore for frictionally clamping an object within the clamping bore. The preferred surgical support structure joint of the present invention additionally includes a second support member, preferably similar to the first support member. The preferred joint also includes a collar encircling the shaft in engagement with the first support member. The camming member preferably comprises a camming pin journaled to the collar through the shaft. The camming pin has an eccentric outer circumferential surface in engagement with the shaft for forcing the collar along the shaft towards the first support member.

DETAILED DESCRIPTION OF THE PREFERRED EMBODIMENTS

Figure 1:
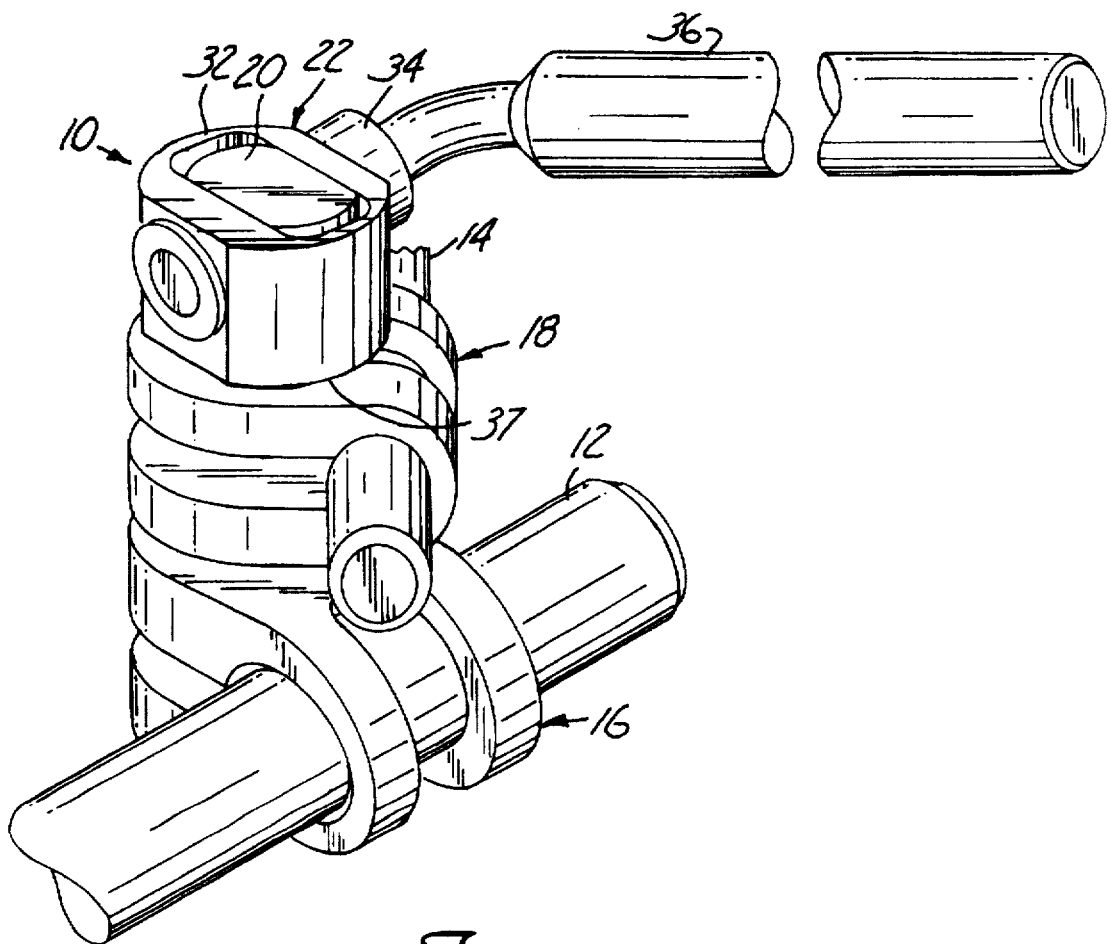
FIG. 1 is a perspective view of a surgical support structure joint of the present invention supporting support rods.

FIG. 1 illustrates surgical support structure joint 10 supporting support rods 12, 14 in one of various positions. Surgical support structure joint 10, exemplifying the present invention, generally includes support members 16, 18, shaft assembly 20 and camming mechanism 22. Support members 16, 18 receive and hold support rods 12, 14, respectively. Preferably, support members 16, 18 releasably clamp about support rods 12, 14, respectively, so as to enable support rods 12 and 14 to be moved and adjusted along and about the axes of support rods 12, 14, respectively, when desired. Alternatively, support members 16, 18 may be fixedly or permanently coupled to support rods 12, 14, respectively.

Support members 16, 18 are pivotally coupled to and about shaft assembly 20. At the same time, each of support members 16, 18 are held in place along the axis of shaft assembly 20. In particular, support member 16 is substantially held in place along the axis of shaft assembly 20 by a retaining member 96 and a spacer 38 (shown in FIG. 2) on opposite sides of support member 16. Support member 18 is substantially held in place along the axis of shaft assembly 20 by spacer 38 (shown in FIG. 2) and camming mechanism 22 on opposite sides of support member 18. Support members 16 and 18 are separated from one another along the axis of shaft assembly 20 by spacer 38 (shown in FIG. 2). Alternatively, support members 16, 18 may abut one another along the axis of shaft assembly 20.

Shaft assembly 20 is an elongate supporting structure extending through support members 16, 18. Shaft assembly 20 pivotally supports support member 16, 18 to permit support members 16, 18 to individually rotate about an axis of shaft assembly 20. As a result, support rods 12, 14 carried by support members 16, 18 may also be positioned in one of a variety of angular positions about the axis of shaft assembly 20.

Camming mechanism 22 includes collar 32, camming member 34 and handle 36. Collar 32 encircles shaft assembly 20 and is coupled to camming member 34. Collar 32 includes a generally flat surface 37 in frictional engagement with a top surface of support member 18 to increase frictional contact between collar 32 and support member 18. Collar 32 abuts support member 18 and retains support members 16 and 18 along shaft assembly 20.

Camming member 34 is journaled to collar 32 through shaft assembly 20. Camming member 34 engages both collar 32 and shaft assembly 20 to move collar 32 and shaft assembly 20 relative to one another along the axis of shaft assembly 20. In the preferred embodiment illustrated, neither collar 32 nor shaft assembly 20 are fixed. However, as can be appreciated, either shaft assembly 20 or collar 32 may alternatively be fixed. Accordingly, if shaft assembly 20 is fixed, actuation of camming member 34 moves collar 32 along the axis of shaft assembly 20. Conversely, if collar 32 is fixed, actuation of camming member 34 moves shaft assembly 20 upward and downward through collar 32.

Actuation of camming member 34 moves collar 32 and shaft assembly 20 relative to one another between a clamped position and an unclamped position. In the clamped position, collar 32 is forced towards retaining member 96 and retaining member 96 is forced towards collar 32 to increase the force and corresponding degree of friction between collar 32 and support member 18 and between support member 16 and retaining member 96. Actuation of camming member 34 also increases the forces and corresponding degree of friction between support members 16 and 18 and spacer 38. Preferably, camming member 34 moves collar 32 and shaft assembly 20 relative to one another so as to sufficiently increase the amount of force and friction between surfaces of members 16 and 18 and adjacent surfaces to prevent unintended rotational movement of support members 16 and 18 about shaft assembly 20. Movement of camming member 34 also compresses support members 16 and 18 about support rods 12 and 14, respectively, to frictionally clamp support rods 12 and 14 in selected rotational and axial positions.

In the unclamped position, collar 32 and retaining member 96 are forced away from one another to decrease the force and corresponding degree of friction between collar 32 and support member 18, between support member 16 and retaining member 96, and between support members 16 and 18 and spacer 38. Preferably, in the unclamped position, camming member 34 sufficiently moves collar 32 and shaft assembly 20 relative to one another to sufficiently decrease the amount of force and friction between surfaces of members 16 and 18 and adjacent surfaces to allow rotational adjustment of support members 16 and 18 about shaft assembly 20. In addition, actuation of camming member 34 into the unclamped position also releases support rods 12 and 14 within support members 16 and 18, respectively, to enable the physician to rotate and reposition support rods 12 and 14 with respect to support members 16 and 18. Thus, camming member 34 moves shaft assembly 20 and collar 32 relative to one another to enable a physician to easily and quickly clamp and unclamp support members 16 and 18 in rotational positions about shaft assembly 20 and to clamp and unclamp support rods 12, 14 in selected rotational and axial positions with respect to support members 16, 18.

In the embodiment illustrated, camming member 34 is moved between a clamped position and an unclamped position by handle 36. Handle 36 is coupled to camming member 34 and provides a lever arm for rotation of camming member 34. In the embodiment illustrated in FIG. 1, handle 36 is generally L-shaped and integrally extends from one side of camming member 34. Once support members 16 and 18 are positioned in a desired rotational orientation about the axis of shaft assembly 20 and once support rods 12 and 14 are also positioned within support members 16, 18 at desired rotational and axial positions, selected actuation of camming mechanism 22 by handle 36 secures and clamps support rods 12 and 14 in their selected positions.

Figure 2:
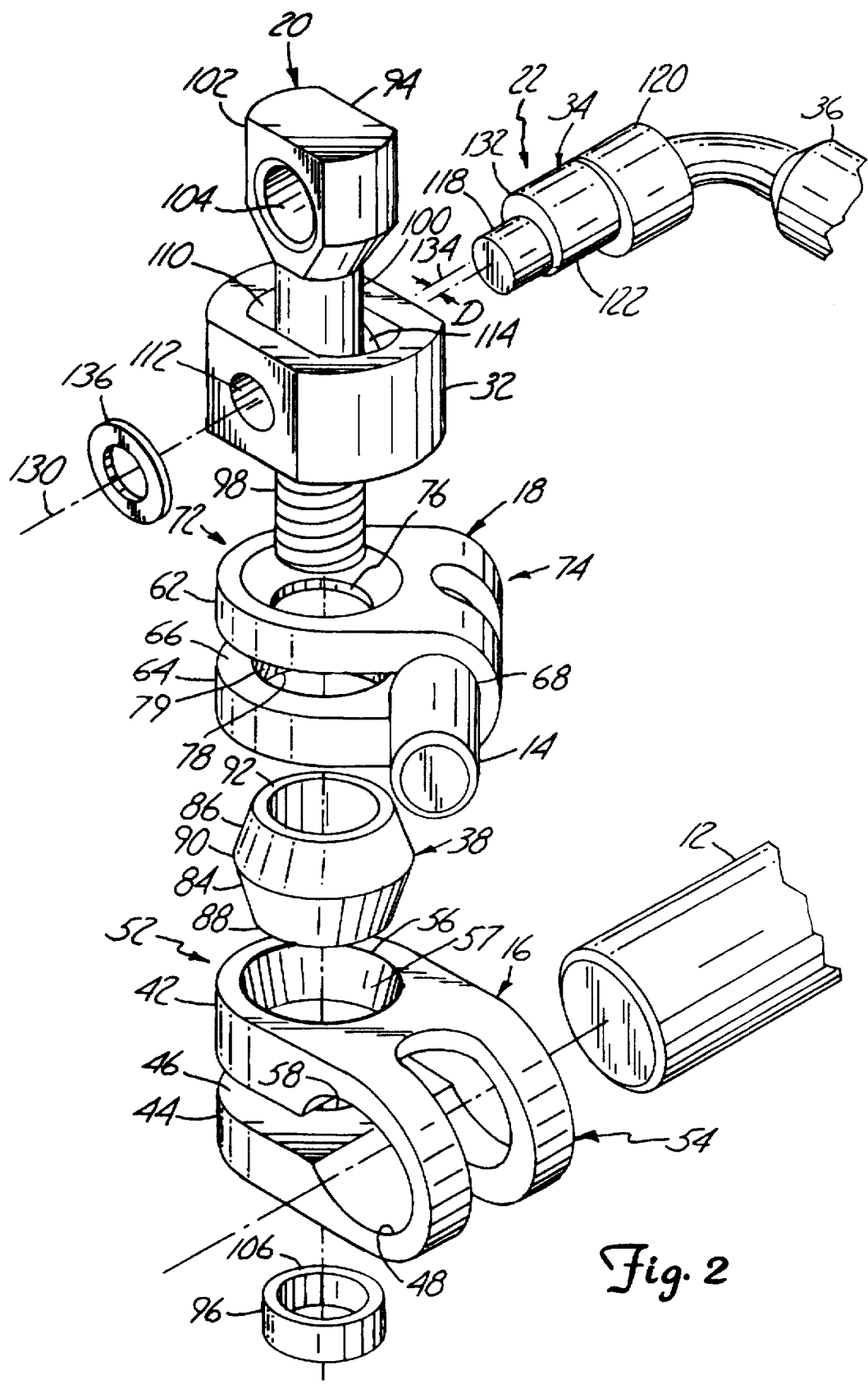
FIG. 2 is an exploded perspective view of the surgical support structure joint of FIG. 1 supporting support rods.

FIG. 2 is an exploded perspective view of joint 10 illustrating support members 16, 18, spacer 38, shaft assembly 20 and camming mechanism 22 in greater detail. As best shown by FIG. 2, support member 16 is a generally U-shaped unitary body including a pair of resilient leg portions 42, 44 separated by slot 46 and clamping bore 48. Slot 46 extends from a first end 52 towards a second end 54 of support structure 16, between leg portions 42, 44 towards clamping bore 48. Clamping bore 48 extends through and between leg portions 42 and 44 and preferably defines a cylindrical-shaped bore sized for receiving support rod 12. Clamping bore 48 preferably has a diameter sized sufficiently larger than a diameter of support rod 12 to enable support rod 12 to be rotationally and axially moved within clamping bore 48 when camming mechanism 22 is in the unclamped position. Leg portions 42 and 44 are sized and are resiliently movable with respect to each other so that the diameter of clamping bore 48 may be reduced sufficiently to frictionally clamp support rod 12 within clamping bore 48 upon actuation of camming mechanism 22. Leg portions 42 and 44 additionally define a pair of aligned pivot bores 56, 58 extending through leg portions 42, 44, respectively, towards first end 52 of support member 16. Pivot bores 56, 58 are sized for receiving shaft assembly 20 to enable support member 16 to pivot about shaft assembly 20. Pivot bore 56 has a counterbore 57, preferably frusto-conical in shape, extending into support member 16 towards slot 46. Counterbore 57 is configured and sized for receiving a corresponding frusto-conical surface of spacer 38. Pivot bore 58 additionally includes a counterbore 89 (shown in FIG. 3) extending into support member 16 towards slot 46. Counterbore 89 is sized for receiving retaining member 96.

Support member 18 is substantially similar to support member 16. Support member 18 includes a pair of resilient leg portions 62, 64 separated from one another by slot 66 and clamping bore 68. Similar to support member 16, slot 66 of support member 18 separates leg portions 62 and 64 and extends from a first end 72 towards a second end 74 of support member 18. Leg portions 62 and 64 further define aligned pivot bores 76, 78. Pivot bores 76 and 78 are aligned with one another and are sized for receiving shaft assembly 20 to enable support member 18 to pivot about shaft assembly 20. Pivot bore 78 has a counterbore 79, preferably frusto-conical in shape, extending into support member 18 towards slot 66. Counterbore 79 is sized for receiving a corresponding frusto-conical surface of spacer 38.

As best shown by FIG. 2, spacer 38 is a generally annular ring encircling shaft assembly 20. Spacer 38 is preferably slidable along shaft assembly 20 so as to forcefully couple support member 16 and 18. As a result, movement of one support member along shaft assembly 20 also moves the other support member for compression or expansion of both support members. Spacer 38 preferably includes opposing frusto-conical surfaces 84, 86. Frusto-conical surface 84 has a lower edge 88 which has an outer diameter smaller than the outer diameter of bore 56 extending through leg portion 42 of support member 16. Frusto-conical surface 84 extends upward towards centerline 90 and widens as it approaches centerline 90. Centerline 90 has an outer diameter larger than the diameter of bore 56. As a result, frusto-conical surface 84 is partially received within counterbore 57 of support member 16 and provides a high level of surface-to-surface contact between support member 16 and spacer 38 for frictionally clamping support member 16 about shaft assembly 20. Frusto-conical surface 86 extends from centerline 90 opposite frusto-conical surface 84 and has a diameter which narrows towards upper edge 92. Centerline 90 has an outer diameter larger than the inner diameter of bore 78 while upper edge 92 has an outer diameter smaller than the inner diameter of bore 78. As a result, frusto-conical surface 86 partially extends into counterbore 79 and engages support member 18 to provide a high degree surface-to-surface contact between spacer 38 and support member 18. Spacer 38 spaces support member 16 from support member 18 and transmits forces along the axis of shaft assembly 20 between support members 16 and 18 for frictionally clamping support members 16 and 18 along shaft assembly 20 in selected rotational orientations.

As further shown by FIG. 2, shaft assembly 20 preferably comprises an elongate retaining bolt 94 and retaining member 96. Bolt 94 includes a threaded end portion 98, an intermediate portion 100 and a head 102. Threaded end portion 98 is externally threaded for threadably engaging retaining member 96. Head 102 of bolt 94 is located opposite threaded end portion 98 and defines bore 104 which extends through head 102 and which is sized for receiving camming member 34. Head 102 is sized for being received within an elongate slot extending through collar 32 of camming mechanism 22.

Retaining member 96 of shaft assembly 20 comprises an annular ring or washer which is fixedly coupled to a lower end of threaded end portion 98 of bolt 94. Retaining member 96 is received within counterbore 89. Retaining member 96 is preferably threaded and swaged onto a lower end of threaded end portion 98 of bolt 94. Retaining member 96 includes a retaining surface 106 which engages and abuts support member 16 to limit vertical movement of support member 16 along the axis of bolt 94 while permitting support member 16 to freely rotate about bolt 94. As can be appreciated, retaining member 96 may have a variety of different configurations or structures having retaining surfaces for allowing rotation of support member 16 while holding support member 16 substantially in place along the axis of bolt 94. For example, bore 58 may alternatively include interior threads which act as retaining surfaces by threadably engaging threaded end portion 98 of bolt 94. Such an alternative arrangement would also permit rotational movement of support member 16 about bolt 94 and would also limit vertical movement of support member 16 along the axis of bolt 94.

As further shown by FIG. 2, collar 32 of camming mechanism 22 defines an elongate slot 110, bore 112 and bore 114. Slot 110 extends through collar 32 along the axis of collar 32 and is sized for receiving head 102 of bolt 94. Preferably, slot 110 has a length longer than a length of head 102 of bolt 94 so as to permit head 102 of bolt 94 to move within slot 110 as collar 32 and bolt 94 are moved relative to one another by camming mechanism 22.

Bores 112 and 114 extend through collar 32 generally perpendicular to slot 110. Bores 112 and 114 extend through opposite sides of collar 32 and are in axial alignment with one another. Bores 112 and 114 are sized for receiving camming member 34 of camming mechanism 22.

As best shown by FIG. 2, camming member 34 is preferably a camming pin including end portions 118, 120 and intermediate portion 122. End portion 118, end portion 120 and intermediate portion 122 are generally cylindrical in shape and are located adjacent to one another. End portion 118 has a diameter sized for being received within bore 112 of collar 32. End portion 120 has a diameter sized for being received within bore 114 of collar 32. End portions 118 and 120 are centered about rotational axis 130 and are journaled within bores 112 and 114, respectively, so as to rotatably support intermediate portion 122 within collar 32 and through bore 104 of bolt 94.

Intermediate portion 122 is eccentrically coupled between end portions 118 and 120. Intermediate portion 122 includes an outer circumferential surface 132 having an axis 134 which is spaced from axis 130 by a distance, D. The distance D separating axis 130 and 134 of end portions 118, 120 and intermediate portion 122 generally determines the maximum distance which camming member 34 moves bolt 94 and retaining member 96 of shaft assembly 20 relative to collar 32. Preferably, the distance D separating axis 130 and 134 is sufficient to frictionally secure support member 16 and 18 about bolt 94 and to clamp support rods 12 and 14 within clamping bores 48 and 68, respectively.

Upon assembly, intermediate portion 122 is located within bore 104 of bolt 94. End portion 118 projects out of bore 112 and is fixedly coupled to retaining washer 136 to rotatably couple and secure camming member 34 through collar 32 and head 102 of bolt 94.

Figure 3:
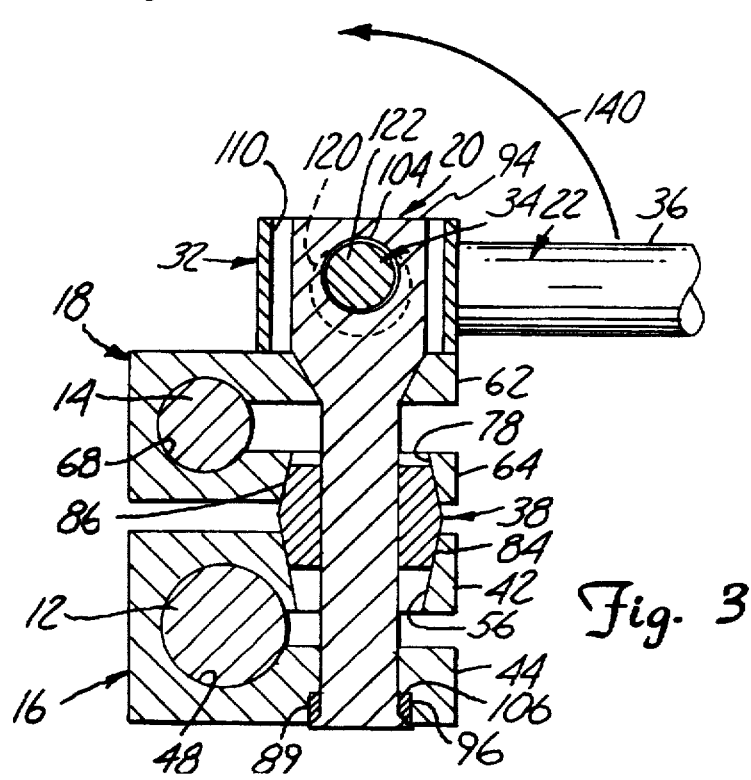
FIG. 3 is a cross-sectional view of the surgical support structure joint and support rods of FIG. 1.

FIG. 3 is a cross-sectional view of joint 10 supporting support rods 12 and 14. As best shown by FIG. 3, bolt 94 extends through collar 32, support member 18, spacer 38, support member 16 and retaining member 96. Head 102 of bolt 94 engages an upper surface of support member 18 while retaining member 96 of shaft assembly 20 engages a lower surface of support member 16 to secure support members 16 and 18 between head 102 and retaining member 96 along the axis of bolt 94. Frusto-conical surfaces 84, 86 of spacer 38 extend into bores 56 and 78 of support members 16, 18, respectively, to space apart and forcefully interconnect support members 16 and 18 so that forces are transferred between support members 16 and 18. At the same time, spacer 38 permits support members 16 and 18 to independently rotate about the axis of bolt 94 prior to clamping actuation of camming mechanism 22. Frusto-conical surfaces 84 and 86 also provide a larger surface area of contact between spacer 38 and support members 16 and 18 to frictionally clamp support members 16 and 18 relative to one another.

Head 102 of bolt 94 is encircled by collar 32. Collar 32 rotatably supports camming member 34 through and across head portion 102 of bolt 94.

As shown by FIG. 3, intermediate portion 122 of camming member 34 extends through bore 104 of bore 94 in close tolerance with the inner circumferential surface of bore 104. Intermediate portion 122 is journaled to collar 32 by end portions 118 and 120 (shown in FIG. 2) and rotates about the axial centerline 130 of end portions 118 and 120. As a result, rotation of handle 36 in the direction shown by arrow 140 rotates intermediate portion 122 about the axial centerline 130 of end portions 118 and 120 to move bolt 94 relative to collar 32 through slot 110. As a result, collar 32 applies a force against support member 18, spacer 38 and support member 16 while retaining member 96 applies a corresponding opposite force to support member 16, spacer 38 and support member 18 to frictionally clamp support members 16 and 18 between retaining member 96 and collar 32 to frictionally secure support members 16 and 18 in a selected rotational orientation about bolt 94. In addition, as collar 32 and retaining member 96 are drawn towards one another by rotation of camming mechanism 22, leg portion 62 is moved towards leg portion 64 and leg portion 44 is moved towards leg portion 42 to compress support members 16, 18 to frictionally clamp support rods 12 and 14 within clamping bores 48 and 68 of support members 16 and 18, respectively. Thus, simple actuation of handle 36 and camming mechanism 22 frictionally clamps support members 16 and 18 in selected rotational orientations about bolt 94 and further frictionally clamps support rods 12 and 14 within support members 16 and 18 in selected rotational and axial positions. Conversely, continued or opposite rotation of handle 36 and camming member 34 moves head portion 102 of bolt 94 relative to collar 32 to move retaining member 96 and collar 32 away from one another to reduce forces frictionally binding support members 16 and 18 to spacer 38, collar 32 and retaining member 96 to allow support members 16 and 18 to be rotatably adjusted about bolt 94 and to allow support rods 12 and 14 to be rotated and axially moved within clamping bores 48 and 68, respectively.

Surgical support structure joint 10 enables a physician to quickly and easily adjust and readjust the rotational positions of support members 16 and 18 as well as the rotational and axial positions of support rods 12 and 14 by simply moving and rotating handle 36 and camming member 34 between a first clamped position and a second unclamped position. As a result, positioning and adjustment of support member 16 and 18 as well as support rods 12 and 14 is simple, quick and does not tie up the physician's hands.

Figure 4:
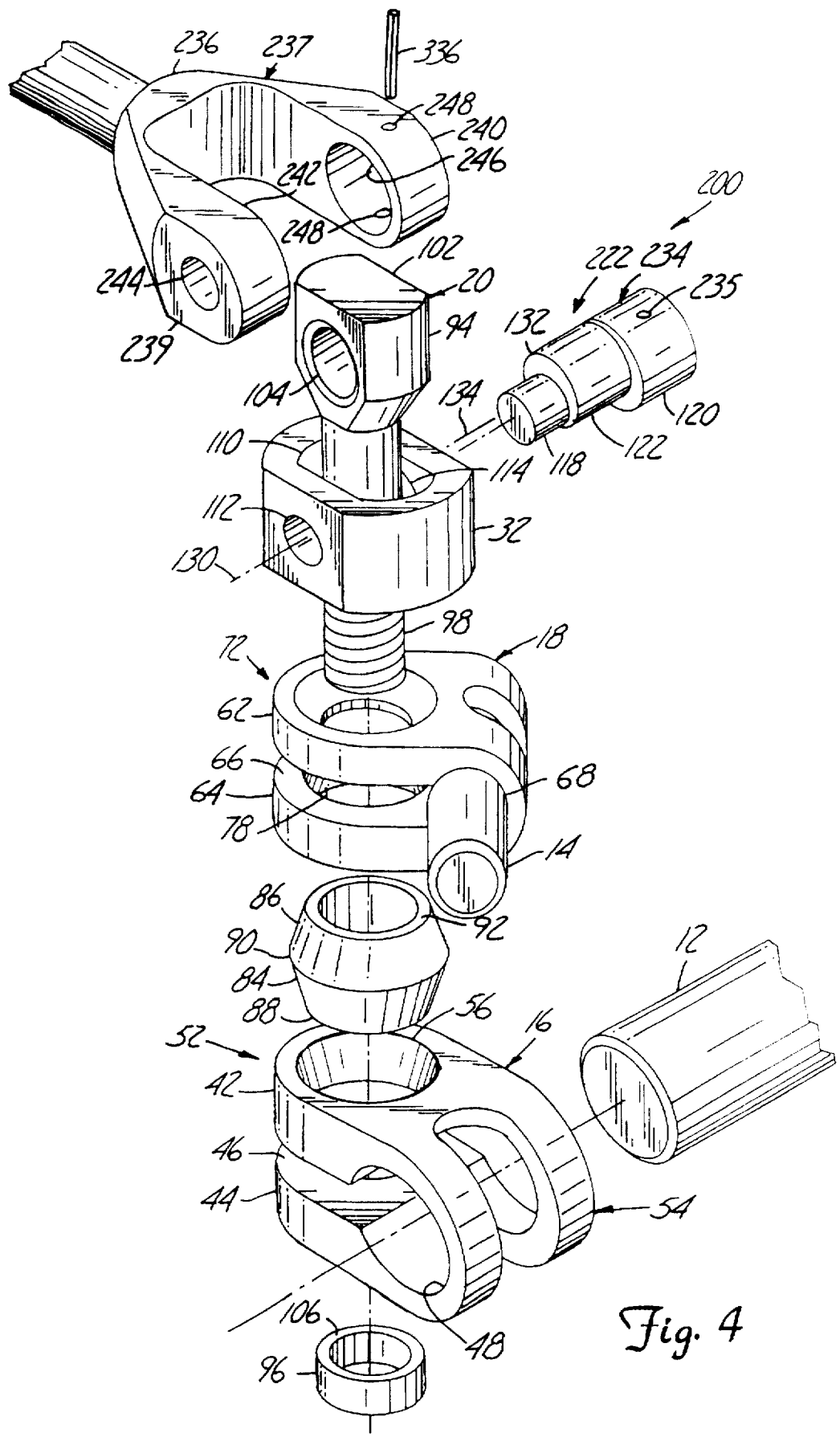
FIG. 4 is an exploded perspective view of an alternate embodiment of the surgical support structure joint of FIG. 1.

FIG. 4 is an exploded perspective view of surgical support structure joint 200, an alternate embodiment of surgical support structure joint 10. Surgical support structure joint 200 is illustrated as supporting a pair of support rods 12, 14. Surgical support structure joint 200 is similar to surgical support structure joint 10 except that surgical support structure joint 200 includes handle 236 in lieu of handle 36, camming member 234 in lieu of camming member 34 and pin 336 in lieu of retaining washer 136. For ease of illustration, the remaining elements of joint 200 which are similar to corresponding elements of joint 10 are numbered similarly. Camming member 234 is similar to camming member 34 except that end portion 120 of camming member 234 includes a pin receiving bore 235 extending through end portion 120. Pin receiving bore 235 is sized for receiving registered pin 336 to couple camming member 234 to handle 236.

Handle 236 is generally an elongate lever arm having a wishbone shaped end 237. End 237 generally includes arm portions 239 and 240 which are separated by slot 242. Arm portion 239 defines bore 244 which extends through arm portion 239. Bore 244 has a diameter sized for receiving end portion 118 of camming member 234. Arm portion 240 defines bore 246 which extends through arm portion 240. Bore 246 has a diameter sized for receiving end portion 120 of camming member 234. Bores 244 and 246 are concentrically aligned with one another. Arm portion 240 additionally defines a pair of aligned bores 248 which have diameters sized for receiving pin 336.

Upon assembly, head 102 of bolt 94 fits within slot 110 of collar 32 so as to align bores 112 and 104. Collar 32 and head 102 of bolt 94 are located within slot 242 of handle 236 so as to further align bores 244 and 246 with bores 112 and 104. Camming member 234 extends through bores 104, 112, 114, 244 and 246. End portion 118 extends across and fits within bores 112 and 244 while end portion 120 extends across and fits within bores 114 and 246. Intermediate portion 122 is located within bore 104 of bolt 94. Once bore 235 is brought into alignment with bores 248 of arm portion 240 of handle 236, registered pin 336 is inserted through and across bores 235 and bores 248 to couple handle 236 to camming member 234.

Handle 236 rotates about axis 130 which concentrically extends through bores 112, 114, 244, 246 and 104. Handle 236 rotates over and about head 102 of bolt 94. As with handle 36, rotation of handle 236 rotates camming member 234 to in turn apply force to support members 16 and 18 so as to frictionally secure and clamp support member 16 and 18 in selected rotational positions about the axis of bolt 94. Continued or opposite rotation of handle 236 causes camming member 234 to apply a smaller degree of force to support members 16 and 18 to permit rotation of support members 16 and 18 about bolt 94 for necessary repositioning of support members 16 and 18 as well as support rods 12 and 14. As with surgical support structure joint 10, surgical support structure joint 200 enables a physician to quickly and easily adjust and readjust the rotational positions of support members 16 and 18 as well as the rotational and axial positions of support rods 12 and 14 by simply moving and rotating handle 236 and camming member 234 between a first clamped position and a second unclamped position. As a result, positioning and adjustment of support member 16 and 18 as well as support rods 12 and 14 is simple, quick and does not tie up the physician's hands.

Joints 10 and 200 of the present invention enable the physician to quickly and easily adjust and readjust the positioning of a retractor coupled to support rods 12 and 14. For ease of illustration, joint 10 has been illustrated as supporting two support rods 12, 14 with two corresponding support members 16 and 18 rotatably coupled between collar 32 and retaining member 96. As can be appreciated, any number of support members and support rods may be located between retaining member 96 and collar 32. For example, joint 10 may alternatively rotatably support a single support member and a single corresponding support rod about the axis of bolt 94. Moreover, as can be appreciated, spacer 38 may be omitted so that support members 16 and 18 directly frictionally engage one another. In addition, additional spacing members such as washers or the like may be utilized along the axis of bolt 94 between collar 32 and retaining member 96.

More notably, camming mechanisms 22 and 222 may have a variety of different configurations, make-up and dimensions. For example, in lieu of intermediate portion 122 of camming members 34 and 234 engaging bolt 94 and end portions 118, 120 engaging collar 32 to move collar 32, bolt 94 and retaining member 96 relative to one another for clamping support members 16 and 18 therebetween, camming mechanism 22 may be configured so as to support a camming surface in direct engagement with support member 18, whereby rotation of the camming member directly applies force to an upper surface of support member 18 to move or force support members 16 and 18 towards a retaining member to frictionally clamp support member 18 and support member 16. Furthermore, although camming members 34 and 234 have been illustrated as having a plurality of cylinders eccentrically coupled to one another, camming members 34 and 234 may alternatively have any one of a variety of camming structures such as irregularly shaped lobes, guidance surfaces, or other well-known camming structures such as actuatable levers or wedges which are capable of moving one member relative to another by simple actuation of the camming structure.

Although the present invention has been described with reference to preferred embodiments, workers skilled in the art will recognize that changes may be made in form and detail without departing from the spirit and scope of the invention.

What is claimed is:

1. A surgical support structure joint comprising:

a shaft having an axis;

a first support member rotatably supported about the axis of the shaft;

a camming member coupled to the first support member, the camming member being movable between a first clamping position and a second nonclamping position, wherein the camming member applies greater force to the first support member in the first clamping position than in the second nonclamping position to prevent rotation of the first support member in the first clamping position and to permit rotation of the first support member in the second nonclamped position; and a collar encircling the shaft in engagement with the first clamping member, wherein the camming member comprises a camming pin journaled to the collar through the shaft and wherein the camming pin includes an eccentric outer circumferential surface in engagement with the shaft for forcing the collar along the shaft towards the first support member.

2. The joint of claim 1 wherein the first support member includes a first leg portion and a second leg portion rotatably supported about the shaft, wherein the first leg portion and the second leg portion define a clamping bore therebetween and wherein the camming member forces the first and second leg portions towards one another in the first clamped position to reduce the diameter of the clamping bore for frictionally clamping an object within the clamping bore.

3. The joint of claim 1 wherein the first support member is a generally U-shaped unitary body including a pair of resilient leg portions, each leg portion defining a pivot bore through which the shaft extends, each leg portion further defining a clamping bore therebetween, wherein the camming member forces the leg portions towards one another in the first clamped position to reduce the diameter of the clamping bore for frictionally clamping an object within the clamping bore.

4. The joint of claim 1 including a second support member rotatably supported about the axis of the shaft and coupled to the camming member.

5. The joint of claim 4 including a spacer between the first support member and the second support member.

6. The joint of claim 5 wherein the first support member and the second support member each include a frusto-conical recess and wherein the spacer includes first and second opposing frusto-conical portions frictionally received within the frusto-conical recesses of the first and second members, respectively.

7. The joint of claim 4 wherein the second support member includes a first leg portion and a second leg portion rotatably supported about the shaft, wherein the first leg portion and the second leg portion define a clamping bore therebetween and wherein the camming member forces the first and second leg portions towards one another in the first clamping position to reduce the diameter of the clamping bore for frictionally clamping an object within the clamping bore.

8. The joint of claim 4 wherein the second support member is a generally U-shaped unitary body including a pair of resilient leg portions, each leg portion defining a pivot bore through which the shaft extends, each leg portion further defining a clamping bore therebetween and wherein the camming member forces the leg portions towards one another in the first clamping position to reduce the diameter of the clamping bore for frictionally clamping an object within the clamping bore.

9. The joint of claim 1 including a handle coupled to the camming member for movement of the camming member between the first clamping position and the second non-clamping position.

10. A surgical support structure joint comprising:
a first support member;
a shaft extending through the support member for pivotally supporting the first support member, the first shaft having a first end and a second end; and
a clamp for clamping the support member in a selected position about the shaft, the clamp including:
a retaining member coupled to the first end of the shaft in forceful engagement with the first support member;
a collar encircling the shaft in forceful engagement with the support member; and
a camming pin journaled to the collar through the shaft, wherein the camming pin includes an eccentric outer circumferential surface in engagement with the shaft for moving the shaft relative to the collar, wherein rotation of the camming pin moves the collar and the retaining member between a first position and a second position relative to one another, wherein the collar and the retaining member frictionally clamp the first support member therebetween to prevent rotation of the first support member in the first position and wherein the collar and the head permit rotation of the first support member about the shaft in the second position.

11. The joint of claim 10 wherein the first support member is a generally U-shaped unitary body including a pair of resilient leg portions, each leg portion defining a pivot bore through which the shaft extends, each leg portion further defining a clamping bore therebetween, wherein the clamp moves the leg portions towards one another in the first position to reduce the diameter of the clamping bore for frictionally clamping an object within the clamping bore.

12. The joint of claim 10 including a handle coupled to the camming pin.

13. The joint of claim 10 wherein the retaining member is fixedly coupled to the shaft.

14. The joint of claim 10 including:
a second support member between the retaining member and the collar, the second support member being pivotally supported about the shaft.

15. The joint of claim 14 wherein the first support member and the second support member each include a frusto-conical recess wherein the joint includes a spacer about the shaft between the first and second members, the spacer having first and second opposing frusto-conical portions frictionally received within the frusto-conical recesses of the first and second members, respectively.

16. The structure of claim 10 wherein the collar includes an elongate slot through which the shaft extends.

17. A surgical support apparatus comprising:
a first clamping member having substantially U-shaped unitary body including a first pair of resilient leg portions, the first pair of leg portions having first aligned pivot bores and defining a first clamping bore between the first pair of resilient leg portions;
a second clamping member having a substantially U-shaped unitary body including a second pair of resilient leg portions, the second pair of leg portions having second aligned pivot bores and defining a second clamping bore between the second pair of resilient leg portions;
a bolt extending through the first and second aligned pivot bores of the first clamping member and the second clamping member, respectively, wherein the first clamping member and the second clamping member pivot about the bolt for supporting a first rod section and a second rod section, respectively, in selected rotational positions about the bolt; and
a camming mechanism for clamping the first rod within the first clamping bore and the second rod within the second clamping bore and for clamping the first and second members in selected rotational positions about the bolt, the camming mechanism including:
a retaining member coupled to the bolt in forceful engagement with the first clamping member;
a collar encircling the bolt in forceful engagement with the second clamping member; and
a camming pin journaled to the collar through the bolt, the camming pin having an eccentric outer circumferential surface which engages the bolt, wherein rotation of the camming pin moves the collar and the retaining member towards one another to clamp the first rod within the first clamping bore, to clamp the second rod within the second clamping bore and to clamp the first and second clamping members between the retaining member and the collar to prevent rotation of the first and second clamping members about the bolt.

18. The support structure of claim 17 wherein the first and second clamping members each include frustro-conical recesses encircling the pivot bore and wherein the structure includes spacer encircling the bolt between the first and second clamping members, the spacer including first and second opposing frustro-conical portions frictionally received within the frustro-conical recesses of the first and second clamping members, respectively.

* * * * *